| (12) | United States Patent | (10) Patent No.: | US 7,960,493 B2 |
|---|---|---|---|
| | Henry et al. | (45) Date of Patent: | Jun. 14, 2011 |

(54) ESTERIFICATION PROCESS OF POLYOLS WITH TERTIARY ALKYL SUBSTITUTED ACIDS

(75) Inventors: Nathalie Solange Jeanne Yvette Henry, Louvain-la-Neuve (BE); Denis Marie Charles Heymans, Louvain-la-Neuve (BE); Griet Uytterhoeven, Louvain-la-Neuve (BE)

(73) Assignee: Momentive Specialty Chemicals Inc., Columbus, OH (US)

( * ) Notice: Subject to any disclaimer, the term of this patent is extended or adjusted under 35 U.S.C. 154(b) by 0 days.

(21) Appl. No.: 12/767,591

(22) Filed: Apr. 26, 2010

(65) Prior Publication Data

US 2010/0240861 A1 Sep. 23, 2010

Related U.S. Application Data

(62) Division of application No. 11/915,218, filed as application No. PCT/EP2006/004070 on May 2, 2006, now Pat. No. 7,737,297.

(30) Foreign Application Priority Data

Jun. 24, 2005 (EP) .................................... 05076468

(51) Int. Cl.
  *C08G 63/02* (2006.01)
  *C08G 63/66* (2006.01)
(52) U.S. Cl. .......................... 528/271; 528/300; 528/301
(58) Field of Classification Search .................. None
  See application file for complete search history.

(56) References Cited

U.S. PATENT DOCUMENTS

| 5,324,853 A | 6/1994 | Jones et al. | |
|---|---|---|---|
| 5,869,191 A * | 2/1999 | Clemons Van Gaalen et al. .............................. | 428/482 |
| 2004/0030168 A1 | 2/2004 | Mozeleski et al. | |

FOREIGN PATENT DOCUMENTS

WO   WO 96/10009 A   4/1996

OTHER PUBLICATIONS

Hexion, Product Bulletin, Cardura E10P A Building Block and Acid Scavenger for Polyesters, 2006, Hexion Specialty Chemicals, Inc., pp. 1-4.*

* cited by examiner

*Primary Examiner* — Paul A Zucker

(57) ABSTRACT

A process to prepare polyol esters from tertiary alkyl acid with reduced homo-polymerisation of the polyols. The ester polyol can be used in the synthesis of further polyester resins for coating or structural/composite or lube oil applications.

16 Claims, No Drawings

ESTERIFICATION PROCESS OF POLYOLS WITH TERTIARY ALKYL SUBSTITUTED ACIDS

CROSS REFERENCE TO RELATED APPLICATIONS

This application is a divisional of U.S. patent application Ser. No. 11/915,218 filed May 15, 2008, now U.S. Pat. No. 7,737,297, which is a 371 application of PCT/EP2006004070 dated May 2, 2006, which claims benefit of European Patent Application No. 05076468.7, filed Jun. 24, 2005, the entire contents of which are hereby incorporated by reference.

SPECIFICATION

The present invention relates to a process to prepare polyol esters from tertiary alkyl acid with reduced homo-polymerisation of the polyols. Esters of trialkyl acetic acids are known to have high hydrolytic resistance, and to enhance the hydrolytic stability of adjacent ester. They are therefore well suitable for coating and or structural end use applications, where resistance against hydrolysis is desired. This property is due to steric hindrance provided by the trialkyl group of the acid. Partially esterified polyols with trialkyl acetic acid are therefore appreciated as building-block in the synthesis of resins for coatings or structural applications.

The esterification of an alcohol with a trialkyl acetic acid is difficult, and therefore such an acid has even been used as catalyst to promote the esterification reaction of a less sterically hindered acid with an alcohol (WO 01 44156).

The use of traditional esterification catalysts for the esterification of a sterically hindered acid with alcohol or polyol is known from Jour. Am. Oil. Chem. Soc., Vol 45, 5-10, January 1968. The conditions used are in the opinion of the authors more rigorous than for non-sterically hindered acid or alcohol and in the case of polyols they worked with an excess of acid to achieve a complete esterification of the alcohol functions.

The esterification of highly branched (sterically hindered) acids was also known by use of non traditional esterification catalysts. The use of chlorosilanes (Bull. Chem. Soc. Jpn, 54, 1267-1268) is efficient in case of a mono alcohol due to the formation of the alkoxysilanes as active species. However, not any technology is given as to the use of this method for partial esterification of polyols.

From said cited publications it can be derived that the prior art solutions suffer from disadvantages such as the use of expensive catalysts, or that the conditions could not be used to promote a partial esterification of a polyol to yield predominantly mono ester of polyols with only small amounts of higher molecular weight compound resulting from etherification side reactions.

A process that could use conventional esterification catalysts to produce predominantly mono-ester of polyols is strongly needed by the industry; as such a monomer is seen as a valuable building block to be used in further resin synthesis.

As result of extensive research and experimentation, it has now surprisingly been found that a selection of specific process conditions in combination with a specific of catalyst enables the predominant formation of low viscosity hydroxyl functional mono-ester from tertiary alkyl carboxylic acids with polyols.

Surprisingly, it has been found now that use of sulfonic acid derivatives under mild thermal conditions is an efficient combination to the production of a mono-ester of a polyol without significant formation of polyethers. Said polyethers are regarded as undesired homopolymer side products and believed to be the reaction product between alcohol functions; this reaction is a competition reaction when esterification is slow or when the alcohol is used in excess over the acid functions. The present invention provides a solution for the problem encountered i.e. an improved selective preparation of mono ester from polyols and sterically hindered carboxylic acids.

The process for the above selective esterification reaction is obtained in the presence of acid catalyst at a temperature below 180° C.

Suitable polyols can be selected from ethylene glycol, propylene glycol, oligomer of glycols (n from 2 to 10), glycerol, neopentyl glycol, trimethylolpropane, pentaerythritol, and combination thereof. In one embodiment, the polyols are selected from ethylene glycol, neopentyl glycol, trimethylolpropane, pentaerythritol. In another embodiment, the polyols are selected from neopentyl glycol, trimethylolpropane.

The acid derivative is selected from an acid corresponding to the general formula (I),

(I)

in which $R^1$ and $R^2$ are independently aliphatic alkyl radicals of 1 to 10 carbon atoms, the total carbon atoms of the three radicals ($CH_3+R^1+R^2$) being 3 to 20. In another embodiment, the total carbon atoms of the three radicals ($CH_3+R^1+R^2$) being 3 to 13.

The acid catalyst is selected from a sulphonic acid derivative such as methane sulphonic, ethane sulphonic, trifluoromethane sulphonic, para toluene sulphonic, xylene sulphonic acids. In one embodiment, the acid catalyst is selected from methane sulphonic acid or para-toluene sulphonic acid. These acids are used in a range of 0.05 to 4 weight % relative to the weight of acid and polyol. In another embodiment, the range is 0.10 to 2.5 weight % on acid and polyol. In one embodiment, the catalyst is methane sulphonic acid.

The hydroxyl ester derived from the above polyol and the alkyl acid of formula (I) can further be used as building blocks in the preparation of a polyester resin with improved chemical resistance.

The resins so obtained are oligomers that may be used advantageously in coating compositions, in compositions for fiber impregnation and for lube oil application.

Test Description and Analytical Methods:
Impact test: ISO 6272-93 (E)
Pendulum damping test (Koenig hardness):
according to ISO 1522-73(E) or DIN 53 157

Methyl ethyl ketone resistance (MEK) summary of the method:

A piece of cotton wool, soaked with MEK, is rubbed over the coating (using a pressure of around 2 kg). If the coating surface has been rubbed one hundred times up and down without showing any damage, the coating is said to be fully cured. If, after x "double MEK rubs", the coating has been destroyed on a full line going from the top to the bottom of the panel, the coating is said to fail after x "double MEK rubs". The MEK resistance was measured on cured coatings.

Viscosity of Newtonian systems using a Brookfield viscometer: ISO 2555-89.

The invention is illustrated in more detail in the following examples, however without restricting its scope to these specific embodiments. All percentages are contents by mass weight and all parts are parts by mass weight, unless expressly stated otherwise.

EXAMPLES

Manufacturing Procedure

A 1 l round-bottomed glass reactor equipped with a stainless steel anchor stirrer, thermocouple, reflux condenser with a Dean Stark and $N_2$-inlet is used. The tertiary alkyl acid and polyalcohol (see Tables 1 and 2 for the composition); with the mole ratio acid/alcohol is 1:1; are charged into the reactor. The reaction is carried out under $N_2$ and constant stirring and heated progressively. At 130° C., the solvent (xylene) and the catalyst are added. The temperature is raised till

- 150° C. when using pivalic acid (V5)
- 170° C. when using the neo-decanoic acid (V10) (VERSATIC 10 acid, ex commercially available from Hexion Specialty Chemicals, Inc., Columbus Ohio).

The temperature is kept constant till the acid value has reached a constant value. At that moment, the reaction is stopped and cooled down.

The scheme below indicates the structure of the products that have been identified by GC-MS analysis (with ionization detection, mode POS-Cl) for the examples based on trimethylol propane(TMP) as polyol. In the analyzed samples no polyethers were found.

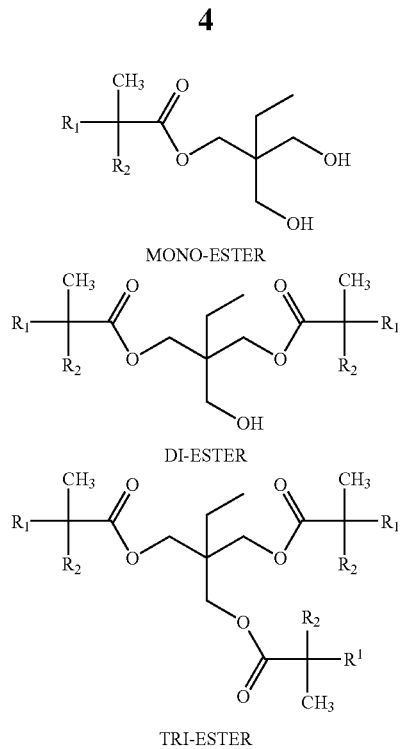

MONO-ESTER

DI-ESTER

TRI-ESTER

The Catalyst Used:
para-toluene sulphonic acid (pTSA)
methane sulphonic acid (MSA 70% in water)

The weight % reported in the Tables below for MSA is the weight of the supplied solution. pTSA supplied as solid, 95.5%, commercially available from Acros Organics, Geel, Belgium MSA supplied as solution (70% in water) commercially available from Atofina, Houston, Tex.

Polyol used as supplied: Trimethylol propane (TMP) 97%, commercially available from Sigma-Aldrich, St. Louis, Mo. Neo pentyl glycol (NPG) 99%, commercially available from Sigma-Aldrich, St. Louis, Mo. Pentaerythritol 98%, commercially available from Sigma-Aldrich, St. Louis, Mo.

Examples of Pivalic Acid (V5)

TABLE 1

|  |  | Example | | | | | | | |
|---|---|---|---|---|---|---|---|---|---|
|  |  | 1 | 2 | 3 | 4 | 5 | 6 | 7 | 8 |
| Acid |  | V5 | V5 | V5 | V5 | V5 | V5 | V5 | V5 |
| Alcohol |  | TMP | TMP | TMP | TMP | TMP | TMP | TMP | TMP |
| molar ratio Alcohol/Acid |  | 1/1 | 1/1 | 1/1 | 1/1 | 1/1 | 1/1 | 1/1 | 1/1 |
| Catalyst |  | pTSA | MSA | MSA | MSA | MSA | MSA | pTSA | pTSA |
| Quantity Cat |  | 2 | 2 | 0.5 | 0.25 | 0.15 | 0.1 | 0.1 | 0.15 |
| Viscosity (mPa · s) |  | 197 | 1818 | 806 | 720 | 450 | 262 | 737 | 420 |
| Colour (Pt/Co) |  | 173 | 324 | 166 | 125 | 73 | 63 | 70 | 118 |
| Time (Hour) |  | 1.5 | 1.5 | 2.5 | 2.5 | 3.5 | 5 | 6 | 5.5 |
| Yield (%)* |  | 95 | 98.5 | 98 | 97 | 97 | 95 | 91 | 98 |
| Ester | Mono | 34 | 66.5 | 63.6 | 68.9 | nd | 74.2 | 73.9 | 70.5 |
| (%) | Di | 59 | 33.5 | 35.7 | 30.7 | nd | 25.6 | 26.1 | 29.5 |
|  | Tri | 7 | 0 | 0.7 | 0.4 | nd | 0.3 | 0 | 0 | nd = not done;

*yield based on converted acid (catalyst intake: all expressed in part by weight on total of acid and polyol weight)

Examples of VERSATIC 10 Acid (V10)

TABLE 2

| Example | Acid | Alcohol | Equivalent ratio Al/Ac | Catalyst Type | Catalyst conc.* | Viscosity [mPa · s] | Colour [Pt/Co] | Reaction time [Hours] | Yield [%] |
| --- | --- | --- | --- | --- | --- | --- | --- | --- | --- |
| 9 | V10 | NPG | 1/1 | pTSA | 2 | 45 | 480 | 6 | 62 |
| 10 | V10 | TMP | 1/1 | pTSA | 4 × 0.5** | 241 | 399 | 12 | 73 |
| 11 | V10 | TMP | 1/1 | pTSA | 2 | / | 450 | 9 | 81 |

**added in four portion over the reaction

Example 12

Polyester Resin Prepared from Ester-Polyol Prepared from Example 6

A 1 l round-bottomed glass reactor equipped with a stainless steel anchor stirrer, thermocouple, reflux condenser and N2-inlet is used. The product of example 6 (177.8 grams) is charged with succinic anhydride (153.6 grams) in the reactor in a 1-1 mole ratio (considering the ideal adduct structure to be the mono ester). The mixture is heated under stirring until 105° C. around this temperature an exotherm occur and the temperature rose till 160° C. The reaction conditions are maintained till the acid value is reached. Then the reaction mixture is cooled down to about 140° C. before adding Cardura E10 (401 gram) the temperature is kept constant for 1 hour.

Polyester Resin Properties:
Color (Pt/Co): 130
Viscosity: 12 690 mPa·s
Coating Formulation
Crosslinker: Cymel 301 commercially available from CYTEC, West Patterson, N.J.
Cure catalyst: pTSA as 40% solution in butanol, concentration 1 weight % on total is used.
Ratio: Polyester 12/Cymel=80/20.
Cure condition of the coated Q panel: 30 minutes 140° C.
Applied layer: 60-65 microns.
Coating Properties:
direct/reverse impact strength>160 inch.lb
Slow penetration 9 mm
MEK resistance>100 double rubs
(MEK=methyl ethyl ketone)

Examples 13 and 14

Polyester Prepared from Pivalic Acid, Polyol and other Acids or Anhydride

The polyesters with the compositions presented in the Table 3 were prepared in a glass reactor equipped with stirrer, heater/cooler and Dean stark. All the ingredients were heated to 160-200° C. until the desired acid value was obtained. Xylene was used to remove the reaction water by azeotropic distillation.

| Ingredients | 13 | 14 |
| --- | --- | --- |
| Pentaerythritol (mole) | 2 | 2 |
| Methyl Hexahydrophthalic anhydride (mole) | 1 | 1 |
| V5 (mole) | 3 | 4 |
| Catalyst | MSA | MSA |
| Catalyst quantity | 0.02 wt % | 0.02 wt % |

-continued

| Ingredients | 13 | 14 |
| --- | --- | --- |
| OH values % | 6.8 | 5.1 |
| MW | 892 | 909 |
| Mn | 722 | 745 |

(V5): pivalic acid

Example 15

Coating Based on Polyester 14

The polyester 14 was then evaluated as reactive diluent for an isocyanate cured coating. It was first blended in 40 wt % with an acrylic polyol. Desmodur N3600, an aliphatic isocyanate from Bayer, was used as curing agent, the catalyst was a mixture of dibutyltin dilaurate and 1,4 diazabicyclo 2,2,2 octane, and the systems were diluted to 100 mPas with butyl acetate.

This system was compared with a similar coating formulation prepared with the acrylic polyol without polyester. The mixture containing 40% had a much lower VOC than the reference material (400 versus 458 g/l) but nevertheless displayed excellent hardening speed and appearance. After less than 30 minutes at 60° C. the system was tack-free.

170° C. when using the neo-decanoic acid (V10)
(VERSATIC 10 acid, ex commercially available from Hexion Specialty Chemicals, Inc., Columbus Ohio).

The temperature is kept constant till the acid value has reached a constant value. At that moment, the reaction is stopped and cooled down.

The scheme below indicates the structure of the products that have been identified by GC-MS analysis (with ionization detection, mode POS-Cl) for the examples based on trimethylol propane(TMP) as polyol. In the analyzed samples no polyethers were found.

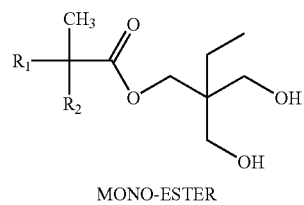

MONO-ESTER

-continued

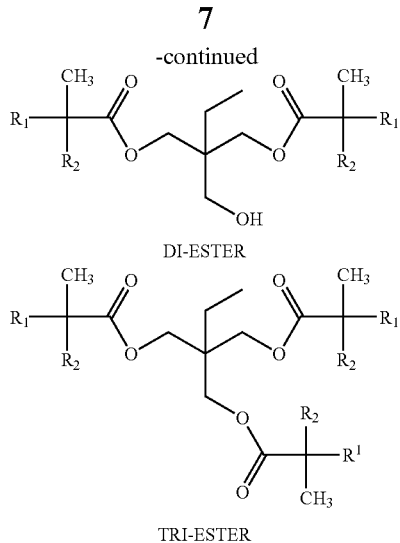

DI-ESTER

TRI-ESTER

The Catalyst Used:
para-toluene sulphonic acid (pTSA)
methane sulphonic acid (MSA 70% in water)
The weight % reported in the Tables below for MSA is the weight of the supplied solution. pTSA supplied as solid, 95.5%, commercially available from Acros Organics, Geel, Belgium MSA supplied as solution (70% in water) commercially available from Atofina, Houston, Tex.
Polyol used as supplied: Trimethylol propane (TMP) 97%, commercially available from Sigma-Aldrich, St. Louis, Mo. Neo pentyl glycol (NPG) 99%, commercially available from Sigma-Aldrich, St. Louis, Mo. Pentaerythritol 98%, commercially available from Sigma-Aldrich, St. Louis, Mo.

The invention claimed is:

1. A resin composition comprising a polyol ester produced by process comprising the steps of reacting a polyol and a tertiary alkyl acid in the presence of an acid catalyst having a pKa from −2 to +2 at a temperature below 180° C., and optionally in presence of an inert organic solvent, wherein the polyol ester is predominantly a mono-ester of the polyol, wherein the acid catalyst is selected from the group consisting of methane sulphonic acid, ethane sulphonic acid, trifluoromethane sulphonic acid, para toluene sulphonic acid, xylene sulphonic acid and combinations thereof, and wherein the polyol is selected from the group consisting of ethylene glycol, propylene glycol, glycol oligomers having 2 to 10 repeating units, neopentyl glycol, trimethylolpropane, pentaerythritol, and combinations thereof.

2. The resin composition of claim 1, wherein the acid catalyst is methane sulphonic acid or para toluene sulphonic acid.

3. The resin composition of claim 1, wherein the acid catalyst is used in a range from 0.05 to 4 weight % relative to the weight of the tertiary alkyl acid and the polyol ester.

4. The resin composition of claim 1, wherein the tertiary alkyl acid is represented by the formula (I),

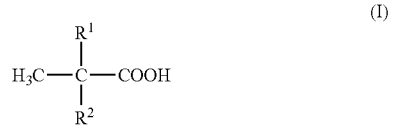

in which $R^1$, $R^2$ are independently aliphatic alkyl radicals having 1 to 10 carbon atoms, and the total carbon atoms of the three radicals of —$CH_3$, $R^1$, and $R^2$, range from 3 to 20.

5. The resin composition of claim 1, wherein the acid catalyst is used in a range from 0.10 to 2.5 weight % relative to the weight of the tertiary alkyl acid and the polyol ester.

6. The resin composition of claim 1, wherein the tertiary alkyl acid is represented by formula (I),

in which $R^1$, $R^2$ are independently aliphatic alkyl radicals having 1 to 10 carbon atoms and the total carbon atoms of the three radicals radicals of —$CH_3$, $R^1$, and $R^2$, range from 3 to 13.

7. A resin composition comprising a polyol ester produced by process comprising the steps of reacting a polyol and a tertiary alkyl acid in the presence of an acid catalyst having a pKa from −2 to +2 at a temperature below 180° C., and optionally in presence of an inert organic solvent, wherein the polyol ester is predominantly a mono-ester of the polyol, wherein the acid catalyst is selected from the group consisting of methane sulphonic acid, ethane sulphonic acid, trifluoromethane sulphonic acid, para toluene sulphonic acid, xylene sulphonic acid and combinations thereof, wherein the polyol is selected from the group consisting of neopentyl glycol, trimethylolpropane, pentaerythritol, and combinations thereof.

8. The resin composition of claim 1, wherein the resin composition comprises a cured resin composition.

9. The resin composition of claim 8, wherein the cured resin composition comprises a shaped article.

10. The resin composition of claim 7, wherein the acid catalyst is methane sulphonic acid or para toluene sulphonic acid.

11. The resin composition of claim 7, wherein the acid catalyst is used in a range from 0.05 to 4 weight % relative to the weight of the tertiary alkyl acid and the polyol ester.

12. The resin composition of claim 7, wherein the tertiary alkyl acid is represented by the formula (I),

in which $R^1$, $R^2$ are independently aliphatic alkyl radicals having 1 to 10 carbon atoms, and the total carbon atoms of the three radicals radicals of —$CH_3$, $R^1$, and $R^2$, range from 3 to 20.

13. The resin composition of claim 7, wherein the acid catalyst is used in a range from 0.10 to 2.5 weight % relative to the weight of the tertiary alkyl acid and the polyol ester.

14. The resin composition of claim 7, wherein the tertiary alkyl acid is represented by formula (I),

in which $R^1$, $R^2$ are independently aliphatic alkyl radicals having 1 to 10 carbon atoms and the total carbon atoms of the three radicals of $—CH_3$, $R^1$, and $R^2$, range from 3 to 13.

15. The resin composition of claim 7, wherein the resin composition comprises a cured resin composition.

16. The resin composition of claim 15, wherein the cured resin composition comprises a shaped article.

* * * * *